(12) United States Patent
Granqvist et al.

(10) Patent No.: US 11,160,453 B2
(45) Date of Patent: Nov. 2, 2021

(54) MULTI-SENSOR SYSTEM FOR ESTIMATING BLOOD PULSE WAVE CHARACTERISTICS

(71) Applicant: Polar Electro Oy, Kempele (FI)

(72) Inventors: Niclas Granqvist, Mägenwil (CH); Patrick Celka, Neuchatel (CH)

(73) Assignee: Polar Electro Oy, Kempele (FI)

( * ) Notice: Subject to any disclaimer, the term of this patent is extended or adjusted under 35 U.S.C. 154(b) by 461 days.

(21) Appl. No.: 16/307,938

(22) PCT Filed: Jun. 9, 2017

(86) PCT No.: PCT/FI2017/050430
§ 371 (c)(1),
(2) Date: Dec. 6, 2018

(87) PCT Pub. No.: WO2017/212120
PCT Pub. Date: Dec. 14, 2017

(65) Prior Publication Data
US 2019/0254524 A1    Aug. 22, 2019

(30) Foreign Application Priority Data

Jun. 10, 2016 (GB) ..................... 1610174

(51) Int. Cl.
*A61B 5/00* (2006.01)
*G16H 20/30* (2018.01)
(Continued)

(52) U.S. Cl.
CPC .......... *A61B 5/0024* (2013.01); *A61B 5/0245* (2013.01); *A61B 5/0261* (2013.01);
(Continued)

(58) Field of Classification Search
CPC .............. A61B 5/0024; A61B 5/02125; A61B 5/02427; A61B 5/02438; A61B 5/0245;
(Continued)

(56) References Cited

U.S. PATENT DOCUMENTS

| 9,591,976 B2 | 3/2017 | Sugo et al. |
| 2008/0249382 A1 | 10/2008 | Oh et al. |

(Continued)

FOREIGN PATENT DOCUMENTS

| CN | 1548005 A | 11/2004 |
| CN | 101006915 A | 8/2007 |

(Continued)

OTHER PUBLICATIONS

Search Report from UKIPO, for related Application No. GB1610174.3 dated Aug. 10, 2016, 2 pgs.

(Continued)

*Primary Examiner* — Mallika D Fairchild
(74) *Attorney, Agent, or Firm* — FisherBroyles, LLP

(57) ABSTRACT

The present document discloses a solution for estimating blood pulse wave characteristics by using multiple measurement locations of a human body. According to an aspect, a method includes detecting, in a first measurement signal measured by a first heart activity sensor associated with a first location of a human body, a first occurrence of a blood pulse wave; detecting, in a second measurement signal measured by a second heart activity sensor from a second location of the human body different from the first location, a second occurrence of the blood pulse wave; estimating, on the basis of said detections synchronized to a common clock, time characteristics of the blood pulse wave; and computing, on the basis of said time characteristics, a metric representing a physiological condition of the human body.

13 Claims, 7 Drawing Sheets

(51) Int. Cl.
*G16H 50/50* (2018.01)
*G16H 50/30* (2018.01)
*A61B 5/021* (2006.01)
*A61B 5/024* (2006.01)
*A61B 5/0245* (2006.01)
*A61B 5/026* (2006.01)
*A61B 5/11* (2006.01)
*G16H 40/63* (2018.01)
*A61B 5/16* (2006.01)
*A61B 5/0205* (2006.01)
*A61B 5/22* (2006.01)
*A61B 5/352* (2021.01)

(52) U.S. Cl.
CPC ...... *A61B 5/02125* (2013.01); *A61B 5/02427* (2013.01); *A61B 5/02438* (2013.01); *A61B 5/1102* (2013.01); *A61B 5/7221* (2013.01); *G16H 20/30* (2018.01); *G16H 40/63* (2018.01); *G16H 50/30* (2018.01); *G16H 50/50* (2018.01); *A61B 5/0006* (2013.01); *A61B 5/0205* (2013.01); *A61B 5/02405* (2013.01); *A61B 5/165* (2013.01); *A61B 5/22* (2013.01); *A61B 5/352* (2021.01); *A61B 5/681* (2013.01); *A61B 5/6803* (2013.01); *A61B 5/6814* (2013.01); *A61B 5/6824* (2013.01); *A61B 5/6829* (2013.01); *A61B 5/6831* (2013.01); *A61B 2503/10* (2013.01); *A61B 2505/09* (2013.01); *A61B 2560/0242* (2013.01); *A61B 2560/045* (2013.01); *A61B 2560/0462* (2013.01)

(58) Field of Classification Search
CPC ... A61B 5/0261; A61B 5/1102; A61B 5/7221; G16H 50/30
See application file for complete search history.

(56) References Cited

U.S. PATENT DOCUMENTS

| | | |
|---|---|---|
| 2010/0081892 A1 | 4/2010 | Sethi et al. |
| 2010/0160798 A1 | 6/2010 | Banet et al. |
| 2012/0310071 A1* | 12/2012 | Nakao ............... A61B 5/4872 600/393 |
| 2014/0015576 A1 | 6/2014 | Fukuda et al. |
| 2014/0249398 A1 | 9/2014 | Morris et al. |
| 2014/0249443 A1* | 9/2014 | Banet ............... A61B 5/746 600/526 |
| 2014/0278220 A1* | 9/2014 | Yuen ............... A61B 5/02427 702/150 |
| 2015/0366469 A1* | 12/2015 | Harris ............... A61B 5/0205 600/301 |
| 2016/0081563 A1 | 3/2016 | Wiard et al. |
| 2016/0089033 A1 | 3/2016 | Saponas et al. |
| 2017/0079591 A1* | 3/2017 | Gruhlke ............... A61B 5/332 |

FOREIGN PATENT DOCUMENTS

| | | |
|---|---|---|
| CN | 102397064 A | 4/2012 |
| CN | 103598876 A | 2/2014 |
| CN | 103784132 A | 5/2014 |
| CN | 103845046 A | 6/2014 |
| CN | 104138253 A | 11/2014 |
| CN | 104173035 A | 12/2014 |
| CN | 104757957 A | 7/2015 |
| KR | 10-2008-0017525 A | 2/2008 |
| WO | 0178599 A2 | 10/2001 |
| WO | 2005/077260 A1 | 8/2005 |
| WO | 2012/021765 A2 | 2/2012 |
| WO | 2015/121689 A1 | 8/2015 |
| WO | 2016/040264 A1 | 3/2016 |
| WO | 2016/053751 A1 | 4/2016 |

OTHER PUBLICATIONS

Thomas et al., "Bio-Watch—A Wrist Watch based Signal Acquisition System for Physiological Signals including Blood Pressure", 36th Annual International Conference of the IEEE Engineering in Medicine and Biology Society, 2014, pp. 2286-2289.

International Search Report and Written Opinion issued by the International Searching Authority in relation to corresponding PCT application No. PCT/FI2017/050430, dated Sep. 14, 2017, 11 pgs.

First Office Action received for Chinese Patent Application Serial No. 201780035649.9 dated Nov. 2, 2020, 28 pages (including English translation).

* cited by examiner

MULTI-SENSOR SYSTEM FOR ESTIMATING BLOOD PULSE WAVE CHARACTERISTICS

CROSS-REFERENCE TO RELATED APPLICATION

This application is a National Stage application of International Application No. PCT/FI2017/050430, filed Jun. 9, 2017, which claims priority to United Kingdom Application No. 1610174.3, filed Jun. 10, 2016, which are incorporated by reference herein in their entirety.

BACKGROUND

Field

The present invention relates to sensor-based heart activity measurements focused non-invasively to a human body.

Description of the Related Art

Variety of sensor are available for measuring characteristics of blood pulse wave non-invasively form a human body. Some sensors measure electrocardiogram (ECG) and, more recently, sensors based on estimation of photoplethysmography (PPG) have emerged. PPG sensors measure the characteristics optically from a skin of the human body. Other sensor-based solutions are also commercially available.

SUMMARY

The present invention is defined by the subject-matter of the independent claims. Embodiments are defined in the dependent claims.

BRIEF DESCRIPTION OF THE DRAWINGS

In the following the invention will be described in greater detail by means of preferred embodiments with reference to the accompanying drawings, in which.

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Figure 1:
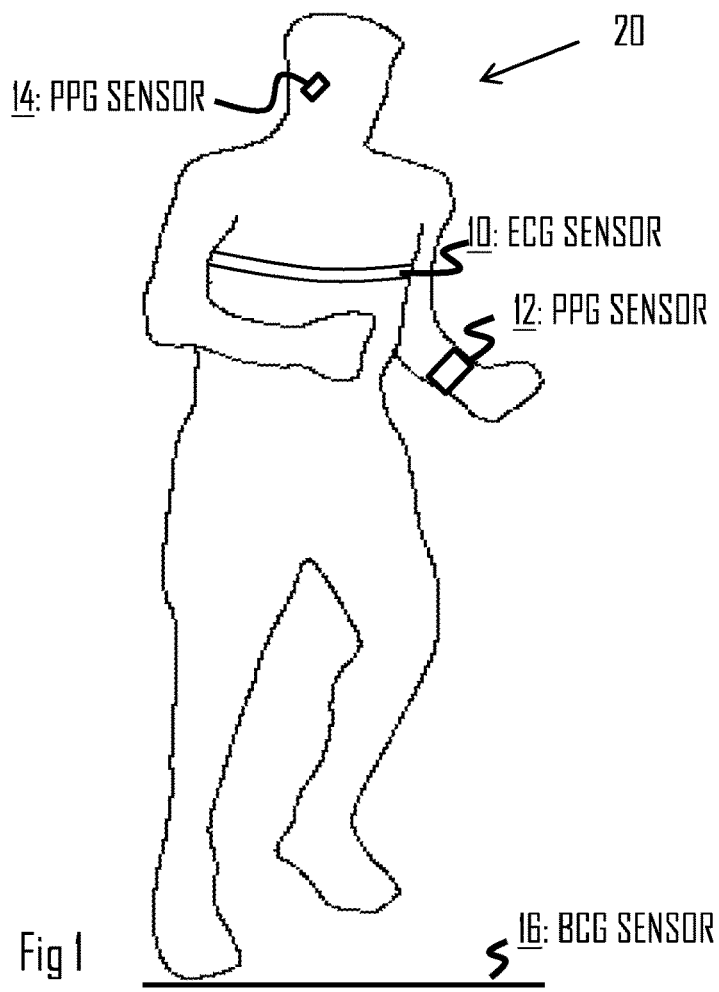
FIG. 1 illustrates a measurement system to which embodiments of the invention may be applied.

FIG. 1 illustrates a measurement system comprising sensor devices that may be used in the context of some embodiments of the present invention. The sensors may employ one or more measurement technologies for measuring heart activity of a user 20. For example, at least one sensor device 10 may be configured to measure electrocardiogram (ECG) of the user 20. Such an ECG sensor 10 may comprise one or more electrodes arranged to be in contact with the user's 20 skin in order to measure electric charges generated during each heartbeat. The ECG sensor may be portable to enable the measurement during an outdoors physical exercise, such as running or cycling.

At least one sensor device 12, 14 may be configured to measure a photoplethysmogram (PPG) optically. PPG represents a volumetric measurement of an organ. A PPG sensor 12, 14 may comprise a light source such as a light emitting diode (LED) configured to illuminate a skin of the user 20 and, further, comprise a light-sensitive sensor such as a photodiode configured to measure changes in light reflected from the illuminated skin. With each cardiac cycle, the heart pumps blood to peripherial arteries. Even though this blood wave pulse is damped by the artery system as it propagates, it is enough to distend arteries and arterioles in the subcutaneous tissue. If the light source and the light-sensitive sensor are place appropriately against the skin, the blood wave pulse can be detected as a change in the reflecting light measured by using the light-sensitive sensor. Each cardiac cycle appears as a peak in a measurement signal acquired through the light-sensitive sensor. The blood pulse wave may be modulated by multiple other physiological systems and, therefore, the PPG may also be used to monitor breathing, hypovolemia, and other physiological conditions. The PPG may be measured at various locations of the human body, e.g. from a wrist (sensor 12), head, ear canal or ear leaf (sensor 14).

At least one sensor device 16 may be configured to measure a ballistocardiogram (BCG). The BCG is a measure of ballistic forces generated during the heartbeat. Ballistocardiogram characterizes motion of the human body resulting from the ejection of blood into the great vessels during each heartbeat. The BCG shows on a frequency range between 1 and 20 Hertz (Hz), and is caused by the mechanical movement of the heart. As the ECG and the PPG, the BCG can be recorded by using a non-invasive sensor 16 from the surface of the body. One The BCG sensor 16 may be a ballistocardiographic scale configured to measure a recoil of the human body standing on the scale. The recoil is caused by the heartbeat and can be measured from the user standing on the BCG scale, e.g. by using a pressure sensor. The BCG scale may be configured to show the user's 20 heart rate as well as weight.

As described above, the blood pulse is modulated on its way through the human body. The modulation may be caused by various physiological conditions and functions. Therefore, characteristics of the blood pulse wave may comprise representation of such physiological conditions. One set of such characteristics may include propagation characteristics of the blood pulse wave. The propagation characteristics may be considered as time characteristics that represent a pulse transit time (PTT), for example, within a certain distance in the human arteries. Equivalent characteristics may include pulse propagation velocity which is proportional to the pulse propagation time and, therefore, can be considered to represent the time characteristics of the blood pulse wave.

Figure 2:
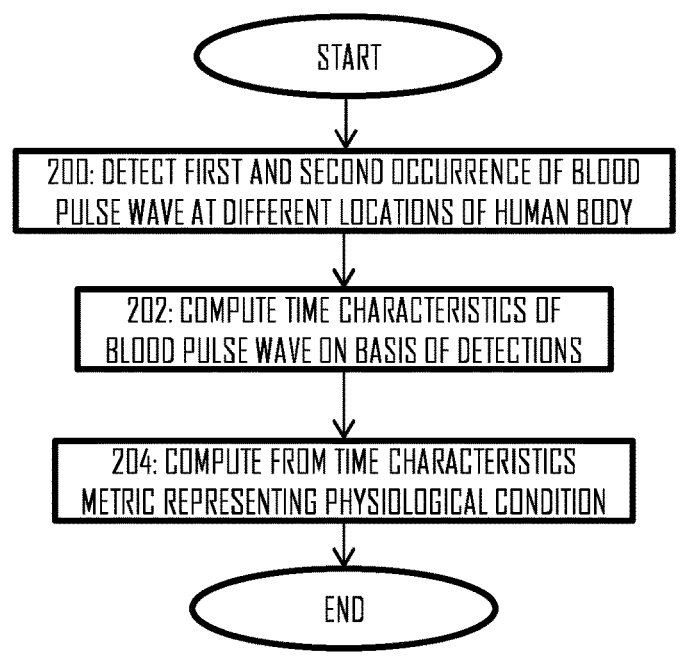
FIG. 2 illustrates a process for estimating physiological condition of a user.

FIG. 2 illustrates an embodiment for evaluating a physiological condition of the user 20. FIG. 2 may be executed in a computer process executed in a computer apparatus. Referring to FIG. 2, the process comprises: detecting (block 200), in a first measurement signal measured by a first heart activity sensor associated with a first location of a human body, a first occurrence of a blood pulse wave; detecting (block 200), in a second measurement signal measured by a second heart activity sensor from a second location of the human body different from the first location, a second occurrence of the blood pulse wave; estimating (block 202), on the basis of said detections synchronized to a common clock, time characteristics of the blood pulse wave; and computing (block 204), on the basis of said time characteristics, a metric representing a physiological condition of the human body.

Since the embodiment of FIG. 2 measures the time characteristics of the blood pulse wave on the basis at least two measurements associated with different locations of the human body, the measurements may be synchronized with each other. When the measurements are carried out by sensors comprised in the same device or the same casing, the measurements may be synchronized by synchronizing the measurements to the same clock signal provided by a clock signal generator of the device. When the measurements are carried out by physically separated sensor devices, e.g. the ECG sensor 10 and the PPG sensor 12, the two devices may be synchronized to a common clock through other means. The synchronization accuracy may depend on precision accuracy required of the computed metric, as described below. One aspect of the synchronization may be seen such that the two detections of the blood pulse wave are made under the same conditions in the sense that they are based on detecting the same component of the blood pulse wave. The component may be the highest peak of the blood pulse wave, the R wave. In the PPG measurements, the R wave may be detected by using a differential measurement signal.

Figure 3:
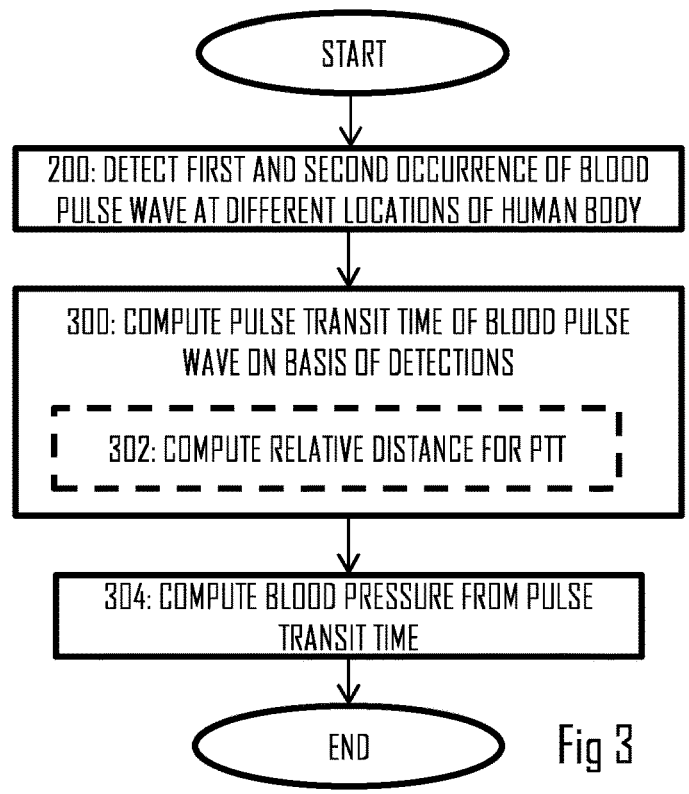
FIG. 3 illustrates an embodiment of FIG. 2.

FIG. 3 illustrates an embodiment where the estimated time characteristics include the pulse transit time (PTT) of the detected blood pulse wave, and wherein the metric represents blood pressure in the human body. It should be appreciated that a metric other than the blood pressure may be computed on the basis of the PTT, as described below. Referring to FIG. 2, the detections of the blood pulse wave described above in connection with block 200 may be used for the estimation of the PTT in block 300. Block 300 comprises computation of the PTT of the blood pulse wave on the basis of said at least two detections of the blood pulse wave associated different locations with different locations of the human body.

In an embodiment, block 300 comprises computing or determining a relative distance associated with the different locations for the PTT computation (block 302). The relative distance may be defined as a difference between a first distance from the first measurement location to the heart of the human body and a second distance from the second measurement location to the heart of the human body. The difference may be determined as an absolute value without a sign. The distance may be considered through a route that travels within the outlines of the human body to represent the distances in terms of the arteries. For example, let us consider two PPG measurements and that the first measurement location is an upper arm of the user and the second measurement location is the user's wrist of the same arm.

Now, the relative distance is the distance between these two locations through the user's arm. In other words, the distance may be considered by using the heart as the reference points and computing a difference between distances to the heart from each location (upper arm and the wrist). Let us then consider that the first measurement is BCG measurement and the first location is the user's foot and that the second measurement is the PPG measurement from the wrist. Now, the first distance is the distance $d_1$ between the foot and the heart, and the second distance $d_2$ is the distance between the wrist and the heart, and the relative distance may be considered as an absolute value of $d_2-d_1$.

Then, let us consider an example where the first measurement is the ECG measurement and the second measurement is the PPG measurement from the wrist. Due to the light-speed propagation of electric signals, the ECG of the blood wave pulse is present everywhere substantially at the same time. Accordingly, no matter where the ECG measurement location is (chest, arm, head, or foot), the location associated with the ECG measurement is the location of the heart. In this case, the first distance may be zero, and the relative distance may equal to the second distance from the human heart.

In some embodiments, there is no need to separately compute the distance but the distance may be preconfigured to the PTT estimation and/or to the computation of the metric. For example, it may be preconfigured to the computation algorithm that the first measurement is the ECG measurement and the second is the measurement from a determined location in the human body in which case the relative distance becomes a constant and needs no separate computation. However, some user-related parameters may be used as an input, e.g. height or gender that may be used to adjust the algorithm to compensate for the different arm or leg lengths of different persons.

In block 304, the blood pressure is computed on the basis of the PTT. It has been discovered, by evaluating average population statistics, that a pulse wave velocity (PWV) and a mean blood pressure (MBP) are mutually proportional as:

PWV≈K MBP+M where K≈0.0825 ms$^{-1}$ mmHg$^{-1}$ and M≈0.0495 m/s can be used as first estimates for the algorithm. These parameters may be re-estimated according to each individual blood pressure profile (calibration). The calibration may be carried out by using a reference system for the blood pressure measurements such as a sphygmomanometer which provides a reference value for the blood pressure. Now, bearing in mind the PWV is proportional to the PTT within the relative distance, we can compute the MBP as $$MBP \approx \frac{D}{KPTT} - \frac{M}{K}$$

Note that the ratios D/K and M/K can be estimated as single parameters during the calibration, thus allowing us to avoid the distance D to be estimated separately. As a result, we have a direct correspondence between the MBP and the PTT and we can determine the MBP by measuring the PTT.

As described above, the blood pulse wave may carry information on various physiological conditions. The PTT may represent, for example, the user's 20 stress level. As a consequence, the metric may be a value or an indicator that represents the user's stress level. Block 204 may thus comprise mapping the measured time characteristics, e.g. the PPT, to such a value or the indicator. The mapping may comprise further inputs such as a heart rate and/or a heart rate variability (variation of consecutive R wave intervals (R-R intervals) of blood pulse waves, and/or a breathing pattern that may be detected through ECG or PPG measurements. In the ECG, the breathing pattern may show in an amplitude component and a phase component of the ECG measurement signal, and the PPG measurement signal may similarly indicate the breathing pattern. In addition to the stress level, the PPT may be used as an indicator of a quality of sleep, aging, fitness level, health state, fatigue estimation (psychological, emotional and physiological), recovery estimation, presence of a sickness such as diabetes, or as an indicator of the user having a habit of smoking. For example, it is known that the blood pressure fluctuations (especially the in the systolic blood pressure) are a function of the mind state of the person and, thus, the PTT is also an indirect measure of this. An embodiment uses the PTT as an input to a stress relieve system such as through a neuro-cardio biofeedback loop incorporating heart rate variability and cardiac coherence, as used in many neuro-rehabilitation devices. Another example is the finer analysis of sleep patterns using the PTT. Indeed, sleep patterns are driven by an oscillation between wake and deep sleep passing through state of dreams. The PTT as a correlate to mind states will thus fluctuate according to the sleep state of the person. Thus variability in the PTT may be considered, as an indicator of the physiological condition of sleep state, e.g. disturbed sleep and associated potentially poorer quality of sleep.

Figure 4:
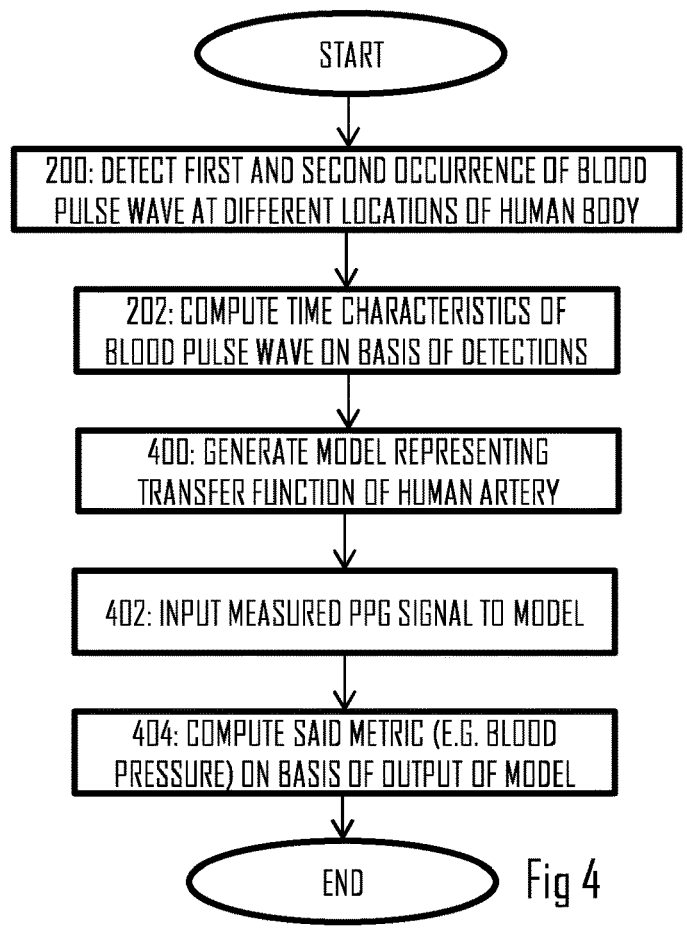
FIGS. 4 to 7 illustrate some embodiments for modelling a human artery system mathematically and for estimating the physiological condition.

In an embodiment, a model characterizing the human artery may be derived on the basis of the measurements, and the model may be used to evaluate the physiological condition(s) of the user 20. Referring to FIG. 4, such an embodiment may comprise after block 202: generating (block 400), on the basis of the time characteristics, a mathematical model representing a transfer function of the user's 20 artery; inputting (block 402) a third measurement signal measured by the second heart activity sensor from the second location, into the mathematical model; and computing (block 404), on the basis of an output of the mathematical model, said metric or another metric representing said physiological condition or another physiological condition of the human body.

Figure 5:
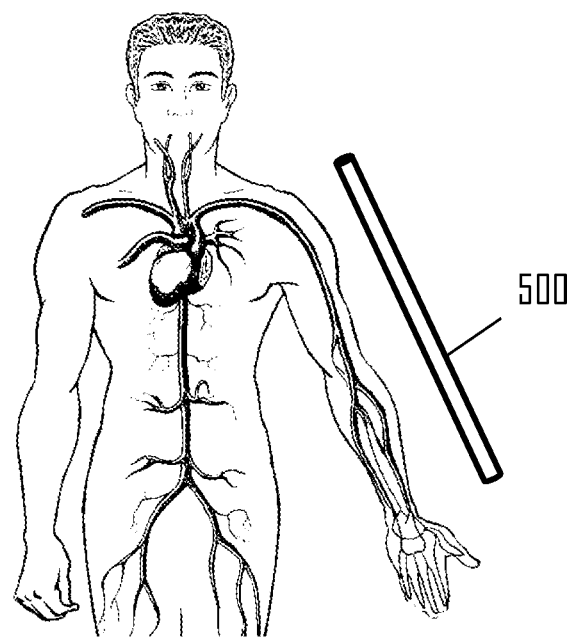
Figure 6:
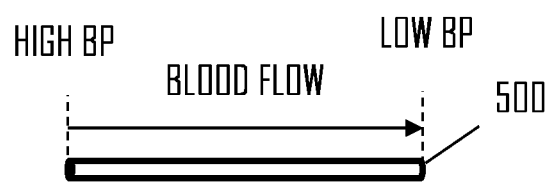
Figure 6:
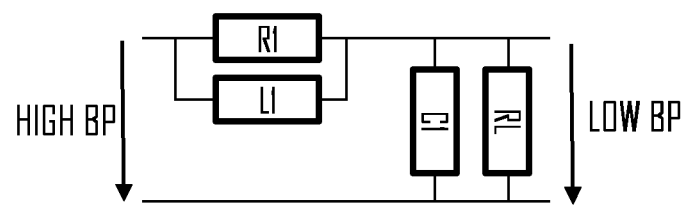
Figure 7:
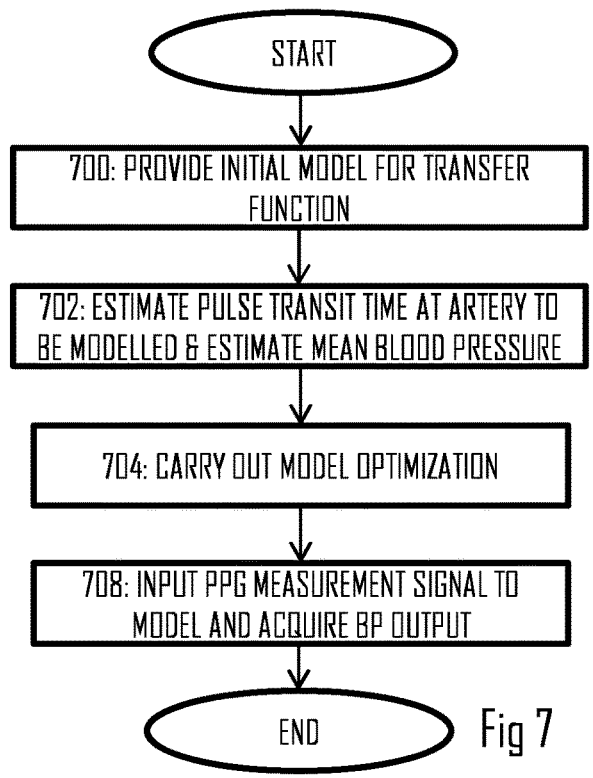

In an embodiment, the mathematical model may comprise a Windkessel model of a filter having characteristics that represent the transfer function of the human artery. Referring to FIGS. 5 and 6, the artery of the human arm is considered. As illustrated with reference to an element 500 modelling the artery visually, the artery filters the blood flow such that the blood pressure (High BP in FIG. 6) at the beginning is higher than the blood pressure (Low BP in FIG. 6) at the end of the artery or a part of the artery under examination. This filtering of the blood pressure by the artery may be modelled with a filter having certain component values. FIG. 6 illustrates a fourth order Windkessel model, wherein component values of the resistors R1 and RL, capacitor C1, and inductor L1 are designed such that the transfer function of the filter matches with the transfer function of the human artery 500. FIG. 7 illustrates an embodiment for building the model.

In an embodiment, the time characteristics determined in block 204, for example, are used in generating a mathematical model representing a transfer function of the human artery. Then, a measurement signal measured by the second heart activity sensor from the second location is applied into the mathematical model and, on the basis of an output of the mathematical model, a metric representing a physiological condition of the human body is computed.

Referring to FIG. 7, the process for generating the model comprises providing an initial model of for the transfer function. The initial model may be a default model generated on the basis of statistical data. The initial model may represent a model of an average human artery. In some embodiments, some input may be used in selecting the initial model amongst a plurality of initial models. The initial models may be configured to represent an average human artery of persons of different ages, and/or genders, for example.

In block 702, the pulse transit time or the time characteristics of the detected blood pulse wave is/are measured and the blood pressure is estimated, e.g. as described above. The second measurement at the second location may in this embodiment be the end point for the artery model, e.g. the wrist, foot, or the ear. The estimated blood pressure may represent the mean blood pressure, for example. Now that the output of the desired model is known, the initial model may be modified on the basis of the blood pressure estimate. Let us consider that the blood pressure estimate represents an input to the artery at the point High BP in FIG. 6. If the transfer function of the model represents the artery, its response to the blood pressure estimate should be a value that is substantially equal to a measurement value at the second location. If the second sensor is a PPG sensor, the measurement value may be a derivative of a measured PPG signal which may be used to detect the peak of the R wave. This may be modelled mathematically as $$d\frac{\widetilde{PPG_0}}{dt} = Z_0 \otimes \widetilde{MBP_0}$$

where $$d\frac{\widetilde{PPG_0}}{dt}$$

represents a time derivative of an estimate of a PPG measurement value, $Z_0$ is the transfer function of the initial model, and $\widetilde{MBP_0}$ is the mean blood pressure estimated in block 702. Now, if $$d\frac{\widetilde{PPG_0}}{dt}$$

differs from the output of the PPG sensor, $Z_0$ may be adjusted on the basis of the difference between the actual output $$d\frac{PPG_0}{dt}$$

of the PPG sensor and $$d\frac{\widetilde{PPG_0}}{dt}$$

such that $$d\frac{\overline{PPG_0}}{dt} - d\frac{PPG_0}{dt}$$

is minimized. The optimization may be realized by using a state-of-the-art system identification algorithm and training data as described in the literature of adaptive filter theory. (block 704). The newly estimated model $\overline{Z_1}$ may then be used to map the measured PPG value to the (mean) blood pressure value through the relation:

$$\widehat{MBP_1} = \overline{Z_1}^{-1} \otimes d\frac{PPG_1}{dt}$$

where $$d\frac{PPG_1}{dt}$$

represents a subsequent measurement value from the PPG sensor (block 708). From the blood pressure value $\widehat{MBP_1}$, an updated PTT may be computed as:

$$\widehat{PTT_1} = \frac{D}{K\widehat{MBP_1} + M}$$

This procedure might be iterated N times until the transfer function parameters have converged to a stable value as measured by the error $$d\frac{\overline{PPG_N}}{dt} - d\frac{PPG_N}{dt}.$$

The PTT may be used to estimate various physiological conditions, as described above. The Windkessel model may be used to estimate the pulse transit time which is proportional to the blood pressure, thus enabling the estimation of the blood pressure of the user 20. As the Windkessel model represents the characteristics of the artery, analysis of the Windkessel model, its parameters, output, and/or transfer function may provide further information on the arteries of the user 20. Analysis of the Windkessel model may, for example, indicate certain syndromes or disorders in the arteries.

As seen from the description of FIG. 7, the embodiment of FIG. 7 computes the PTT from two different starting points (block 702 and block 708). In an embodiment, the measurement of the PTT carried out in block 702 without the model and through the model are combined to provide a more accurate estimate of the PTT. The combining may be carried out by averaging the PTT estimates or selecting one of the estimates according to a determined selection logic, e.g. based on their statistical distribution. One can for example use principal component analysis or probabilistic data fusion method such as Bayesian inference.

Figure 8:
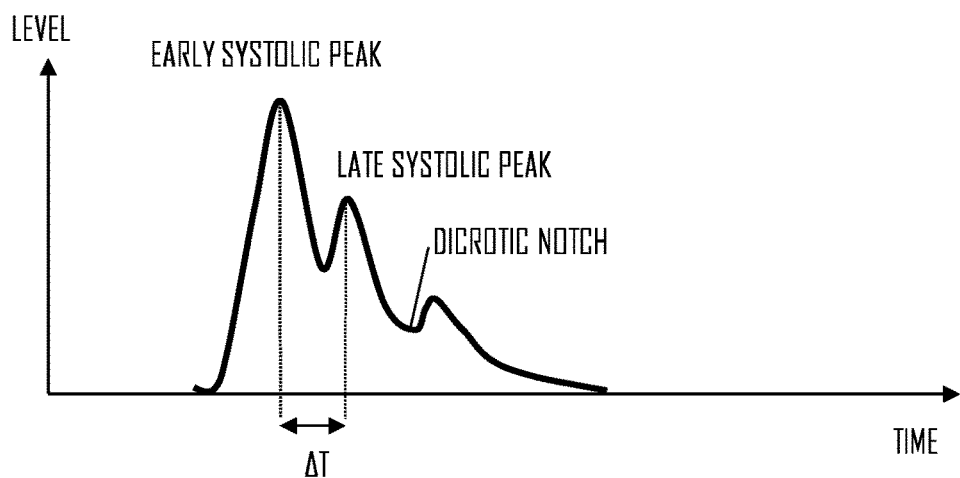
FIGS. 8 and 9 illustrate an embodiment for estimating a pulse transit time of a blood pulse wave.
Figure 9:
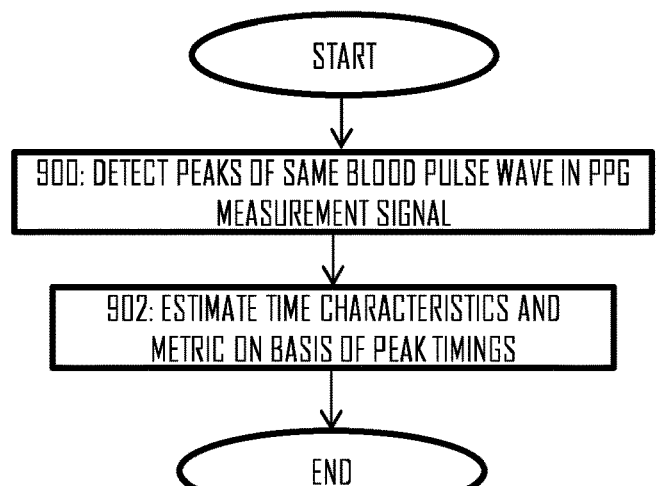

FIGS. 8 and 9 illustrate a further embodiment for estimating the PTT or, in general, the time characteristics of the blood pulse wave. This embodiment utilizes the appearance of multiple signal features of the blood pulse wave in a PPG measurement signal. Referring to FIG. 8 illustrating the PPG measurement signal, the PPG measurement signal typically comprises two peaks: an early systolic peak and a following late systolic peak. The early systolic peak is formed mainly by a pressure transmitted along a direct path from the left ventricle to the measurement location where it generates a change in blood volume. The second peak is formed in part by a pressure transmitted along the aorta and large arteries to sites of impedance mismatch in the body, where it is reflected back up the aorta. It has been discovered that the time difference between the timings of the early and late systolic peaks is proportional to the PTT. FIG. 9 illustrates an embodiment for computing the PTT by using this feature. Also, the condition of the arteries such as their stiffness influences the PTT. The stiffness index may be estimated and used as an input in the estimation of the blood pressure from the PTT. The stiffness is usually estimated using a peripheral augmentation index (PAI) which may be defined as a ratio of the late and early systolic blood pressure as shown in FIG. 8.

Referring to FIG. 9, the process comprises measuring a PPG measurement signal by using a PPG sensor; detecting (block 900), on a basis of a peak detection, a first and a second peak associated with the same blood pulse wave; and estimating (block 902) the time characteristic of the blood pulse wave further on the basis of the detected first and the second peak. The peak detection may be based on monitoring the derivative of the PPG measurement signal and detecting a determined type of change in a sign of the derivative, or using a threshold-based peak detection. The threshold may be fixed or adaptive. In an embodiment, the time difference between the peaks is mapped to the time characteristics by using a mapping table stored beforehand.

One method of detecting the correct peaks may be based on first detecting a timing of a dicrotic notch in the PPG measurement signal. The dicrotic notch may be considered as the last notch in the PPG measurement signal before the signal representing the blood pulse wave fades. Therefore, it may be used as an accurate reference point for determining the early and late systolic peaks (The first and the second peak). The first and the second peak may be determined to be the first two peaks that precede the dicrotic notch.

The embodiments of FIGS. 8 and 9 may be combined with the other embodiments in a straightforward manner. For example, when combining the embodiment of FIG. 9 with the embodiment of FIG. 2, multiple (e.g. two) measurement samples of the PTT or another measured time characteristic is acquired, and the time characteristics may be estimated on the basis of these samples.

In an embodiment, accuracy of each of the multiple samples is computed and more weight is assigned to a more accurate sample, and less weight is assigned to a less accurate sample. The accuracy may be based on motion detection, for example. In connection with a PPG sensor, typically a motion sensor is employed. The motion sensor may be used to carry out motion compensation for a measured PPG signal in order to reduce noise from the PPG signal. The motion sensor may also be used to estimate the accuracy of the measurements. Higher measured motion may be associated with less accurate measurements, while lower measured motion may be associated with more accurate measurements.

In an embodiment, one of the multiple samples is selected as the time characteristics, e.g. based on the estimated accuracy.

In another embodiment, the multiple samples are combined according to a determined combining logic. The combining logic may be averaging or weighted averaging of the multiple samples, for example. The weighting may be based on the accuracy estimation.

Figure 10:
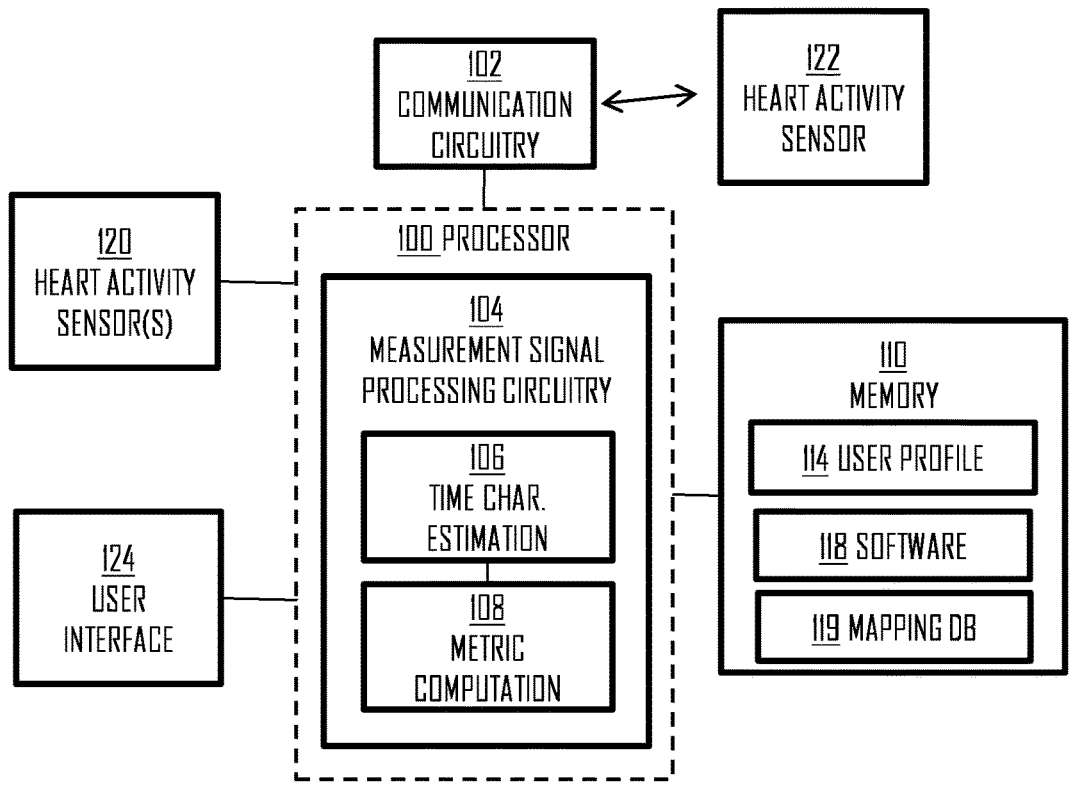
FIG. 10 illustrates an apparatus according to an embodiment of the invention.

FIG. 10 illustrates an embodiment of an apparatus configured to carry out at least some of the above-described functions in determining the time characteristics of the detected blood pulse wave. The apparatus may comprise an electronic device comprising at least one processor 100 and at least one memory 110. The processor 100 may form or be a part of a processing circuitry. The apparatus may further comprise a user interface 124 comprising a display screen or another display unit, an input device such as one or more buttons and/or a touch-sensitive surface, and an audio output device such as a loudspeaker. In some embodiments, the user interface 124 comprises a haptic output device configured to provide haptic indications to the user 20.

The processor 100 may comprise a measurement signal processing circuitry 104 configured to estimate the time characteristics and/or the metric representing the physiological condition. The measurement signal processing circuitry 104 may comprise a time characteristics estimation circuitry 106 configured to estimate the time characteristics such as the PTT from received detected measurement signals. Accordingly, the time characteristics estimation circuitry 106 may be configured to carry out steps 200, 202, 300, 702, 900, and/or a part of 902. The time characteristics estimation circuitry 106 may output the time characteristics such as the PTT to a metric computation circuitry 108 configured to compute the metric at least partially on the basis of the received PTT. The metric computation circuitry 108 may be configured to execute an algorithm receiving the time characteristics as an input. Further input may comprise user characteristics such as an age, gender, height, and weight. The memory 110 may store a database 114 storing a user profile. The functions of the algorithm may be defined by a computer program code 118 stored in the memory. In some embodiments, the algorithm may map the received value or values representing the time characteristics to the metric by using a mapping database 119 stored in the memory. The mapping database may define a correlation between the time characteristics and the metric representing the physiological condition. In an embodiment, the mapping database may define mappings between the PTT and the blood pressure. The mapping database 119 may store a mapping table adapted to the user characteristics. The metric computation circuitry 108 may be configured to carry out steps 204, 304, 404, and/or the metric estimation in block 902.

In an embodiment, the metric computation circuitry 108 is configured to generate the Windkessel model, thereby executing blocks 400, 402, and 404 and/or blocks 702 (the blood pressure measurement), 704, 706, and 708.

Upon successful computation of the metric such as the blood pressure, the metric computation circuitry 108 may output an indicator to the processor 100 or to the user interface 124 and, thus, cause indication about the measured metric to the user. The indicator may be a display indicator displayed on the display unit of the user interface 124, an audio output, or a haptic output.

The apparatus may comprise a communication circuitry 102 connected to the processor 100. The communication circuitry may comprise hardware and software suitable for supporting Bluetooth® communication protocol such as Bluetooth Smart specifications. It should be appreciated that other communication protocols are equivalent solutions as long as they are suitable for establishing a personal area network (PAN) or suitable for measurement scenarios described in this document. The processor 100 may use the communication circuitry 102 to transmit and receive frames according to the supported wireless communication protocol. The frames may carry a payload data comprising the above-described measurement data such as ECG measurement data and/or PPG measurement data. In some embodiments, the processor 100 may use the communication circuitry 109 to transmit the measurement data, estimated time characteristics and/or the computed metrics to another apparatus, e.g. to a cloud server storing the user's 20 user account.

In an embodiment, the apparatus comprises at least one heart activity sensor 12. The heart activity sensor(s) 12 may comprise one or more of the above-described sensors such as an ECG sensor 10, PPG sensor 12, 14, and the BCG sensor 16. Additionally, the apparatus may communicate with at least one heart activity sensor 14 through the communication circuitry 102. The at least one heart activity sensor 14 may comprise an external heart activity sensor with respect to the apparatus. The heart activity sensor(s) 14 may comprise different or different type(s) heart activity sensor(s) than the sensor(s) 12. Table 1 below illustrates some embodiments of heart activity sensor combinations that can be used in the estimation of the above-described metric(s).

TABLE 1

| Heart Activity sensor 1 | Heart Activity sensor 2 |
|---|---|
| PPG sensor 12 wrist | PPG sensor 14 ear, forehead, chest, arm, leg or ankle |
| PPG sensor 12 or 14 wrist, ear forehead, chest, arm, leg, or ankle | ECG sensor 10 |
| PPG sensor 12 or 14 wrist, ear forehead, chest, arm, leg, or ankle | BCG sensor 16 |

In embodiments where the heart activity sensors 12, 14 are provided in different, physically separate devices, the devices may be synchronized to a common clock such as a clock of Global Positioning System or another satellite navigation system providing an accurate clock signal for both devices. Some wireless communication protocols provide synchronization tools, and some embodiments may use such tools to carry out the synchronization. One of the devices may operate as a master clock and it may transmit a frame indicating its clock value to the other device(s), thereby providing clock synchronization. When the devices have synchronized clocks, a sensor device detecting the blood pulse wave may store a clock value associated with the detection, generate a time stamp representing the clock value, and transmit the time stamp to the other device that uses the time stamp in the computation of the time characteristics of the detected blood pulse wave. The other device may associate the timing indicated by the received time stamp with the closest timing of a detection of the blood pulse wave detected by a heart activity sensor comprised in the other device and, as a result, compute the time characteristics of the blood pulse wave detected by both devices.

In another embodiment, instead of using a radio frame to relay the indication of the detected timing of the blood pulse wave, bio impedance may be used. In this embodiment, a first device detecting the blood pulse wave may output an electric signal to the user's skin at the timing of detecting the blood pulse wave. A second device may receive the electric signal through an electrode also attached to the user's skin and, thus, acquire the "time stamp" transferred by using the bio impedance.

Figure 11:
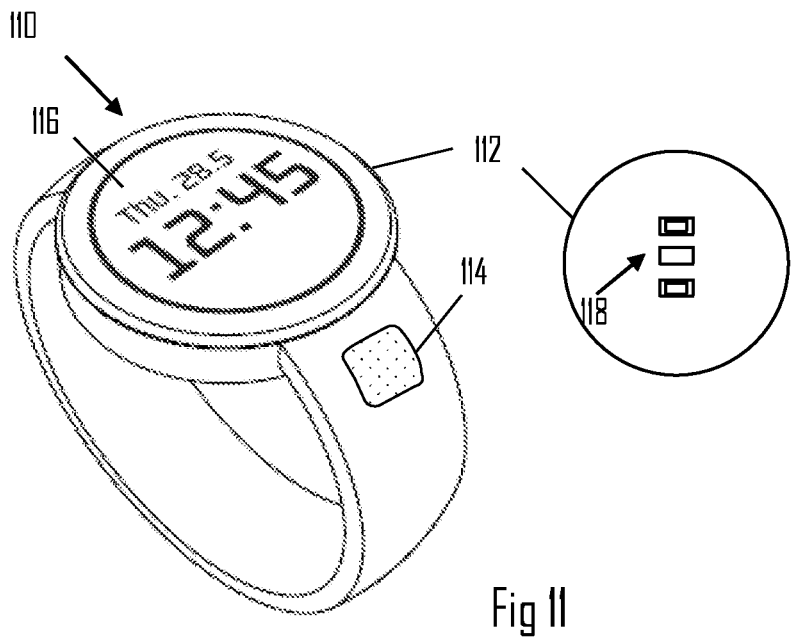
FIG. 11 an embodiment of a wrist computer comprising two heart activity sensors.

Let us now describe some embodiments of the apparatus. In an embodiment, the apparatus is a wrist computer comprising the PPG sensor 12 and, in some embodiments, the ECG sensor. FIG. 11 illustrates an embodiment of the wrist computer 110 comprising the PPG sensor 12 and the ECG sensor. In this embodiment, the PPG sensor and the ECG sensor may be provided on opposite sides of the apparatus, e.g. on surfaces facing opposite directions. Referring to FIG. 11, the PPG sensor may be provided on a surface of a casing 112 of the wrist computer. The casing 112 may house the electronics of the wrist computer such as the processor 100. The surface comprising the PPG sensor may be a surface arranged to face the user's 20 skin when the apparatus is attached to the user, e.g. to the user's wrist. The PPG sensor may comprise a set of optical components 118 comprising at least one illuminating device and at least one optical sensing device. The right hand side of FIG. 11 illustrates the surface of the casing 112 comprising the optical components such that the optical sensing device is provided between two optical illuminating devices. The ECG sensor may be provided on a surface of the apparatus that faces a direction away from the user's skin, when the apparatus is attached to the user 20. In an embodiment, the ECG sensor 114 is attached to a strap of the apparatus, the strap being designed to attach the apparatus to the user 20. In another embodiment, the ECG sensor or at least an electrode of the ECG sensor is provided on the display screen 116 comprised in the casing 112. The electrode of the ECG sensor may then be realized by a transparent film provided on the display screen. In this embodiment, the user 20 may bring his/her finger to the ECG sensor to measure the time characteristics and the metric. In this connection, the above-described indication of the successful computation of the metric may indicate to the user that the user 20 may withdraw the finger from a sensing head of the ECG sensor.

In an embodiment, the apparatus is the wrist computer comprising the PPG sensor 12 and receives the ECG measurement signal from the ECG sensor 10 comprised in a casing attached to the user's chest, for example.

In an embodiment, the apparatus is a headset arranged to be attached to the user's 20 head. The headset may comprise an earpiece.

In an embodiment, the apparatus is a scale comprising the BCG sensor.

In embodiments where the apparatus comprises the PPG sensor, the apparatus may also comprise a motion sensor. The motion sensor may be used to compensate for motion artefacts in the PPG measurement signal.

Figure 12:
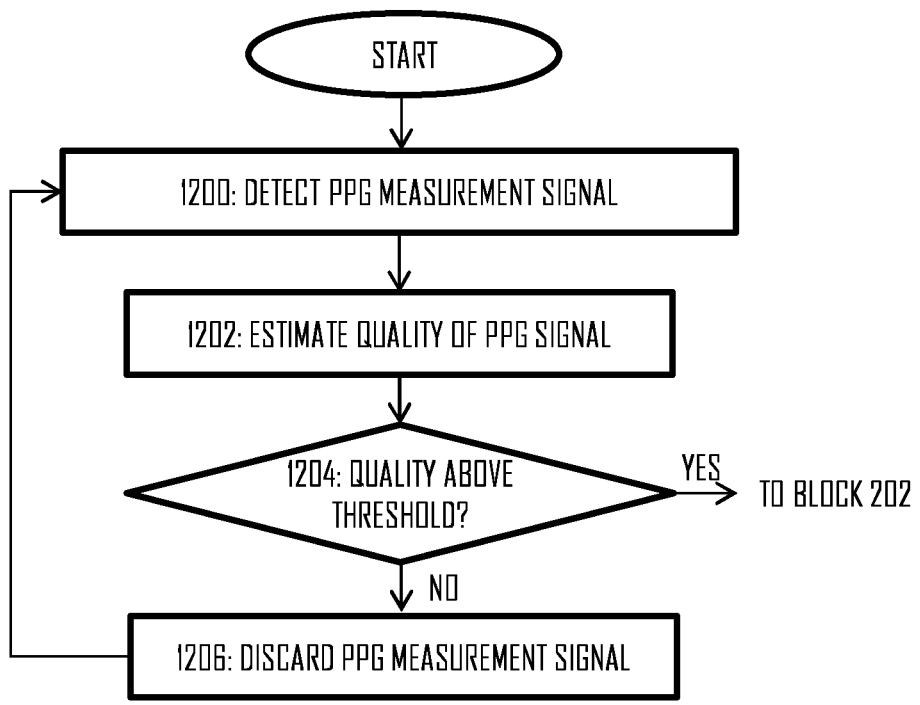
FIG. 12 illustrates a process for estimating a signal quality of a detected measurement signal according to an embodiment of the invention.

In an embodiment, the apparatus comprising the PPG sensor may employ a measurement signal evaluation procedure to estimate whether or not the detected PPG measurement signal is suitable for estimating the time characteristics. FIG. 12 illustrates an embodiment of such a procedure. Referring to FIG. 12, upon detecting a PPG measurement signal in block 1200, e.g. a signal component representing the blood pulse wave, the quality of the measured PPG signal is estimated in block 1202. The estimation may comprise attempting detection of the dicrotic notch of FIG. 8, estimating a signal level, estimating a level of the measurement signal, and/or estimating a number of detected peaks in the measurement signal. Other quality metrics may be employed in other embodiments. In block 1204, the estimated quality metric is compared with a threshold. If the signal quality is determined to be better than the threshold (yes in block 1204), the measurement signal may be passed to the estimation of the time characteristics in block 202. Otherwise (no in block 1204), the measurement signal may be discarded and the process may wait for the subsequent detection of a measurement signal. This improves the reliability of estimating the metric in block 204.

In an embodiment where the apparatus is a wrist computer, the apparatus comprises an altimeter configured to measure an altitude of the apparatus. The altimeter may comprise a barometer. The processor may be configured to compute the metric (e.g. the blood pressure) under a condition where the user's hand is at a determined height with respect to the user's heart, e.g. at substantially the same level. The altimeter may be used to determine the presence of such conditions, thereby improving the accuracy of the estimation. FIG. 12 illustrates an embodiment of a procedure for using the altimeter to determine the correct measurement conditions for measuring the metric such as the blood pressure.

Figure 13:
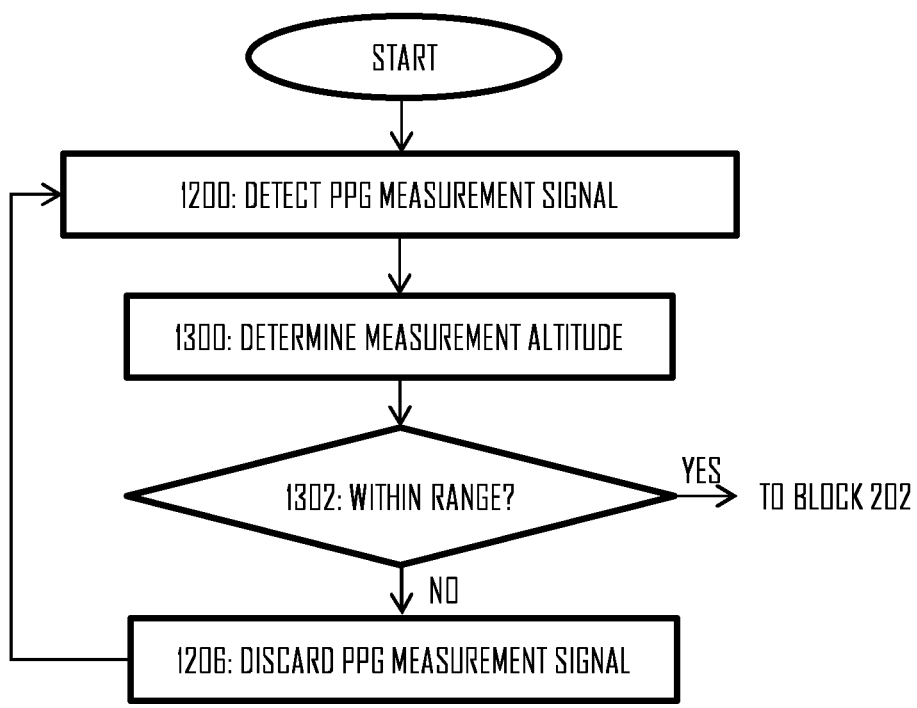
FIG. 13 illustrates a process for estimating measurement conditions of a detected measurement signal according to an embodiment of the invention.

Referring to FIG. 13, the PPG measurement signal is detected in block 1200 by using the PPG sensor of the wrist computer. The detection in block 1200 may comprise detection of the blood pulse wave. The detection may trigger the processor to determine the current altitude by using the altimeter in block 1300. In block 1302, the processor checks whether or not the determined current altitude matches with a reference altitude representing the conditions to which the metric computation has been calibrated. If the determined altitude is within a determined range of the reference altitude in block 1302, the process may proceed to block 202. Otherwise, the measurement signal may be discarded in block 1206.

In an embodiment, the reference altitude may be received from a device attached to the user's chest. The device may also comprise an altimeter. In an embodiment where the device comprises the ECG sensor, the device may transmit the reference altitude to the wrist computer in connection with transmitting a message indicating the detection of the blood pulse wave in the device. The wrist computer may then use the received reference altitude in block 1302. The two altimeters may be calibrated with respect to each other periodically in a calibration phase. The user may be instructed to bring the devices to the same altitude, e.g. to bring the wrist computer to touch the chest device. Then, one of the devices may transmit its altitude to the other device, and the other device may calibrate its altimeter to show the same altitude.

The algorithm mapping the PTT or other time characteristics to the blood pressure or another metric may also be calibrated from time to time. The calibration may use a medical grade blood pressure device prior to breakfast after the night sleep. The user would thus perform the measurement while in bed or sitting with arm at the level of the heart and enter the systolic and diastolic pressures in the wrist unit 110 or via any other connected computing units such as mobile smart phone, tablet or computer.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

In an embodiment, at least some of the processes described in connection with FIGS. 2 to 13 may be carried out by an apparatus comprising corresponding means for carrying out at least some of the described processes. Some example means for carrying out the processes may include at least one of the following: detector, processor (including dual-core and multiple-core processors), digital signal processor, controller, receiver, transmitter, encoder, decoder, memory, RAM, ROM, software, firmware, display, user interface, display circuitry, user interface circuitry, user interface software, display software, circuit, and circuitry. In an embodiment, the at least one processor 100, the memory 110, and the computer program code 118 form processing means or comprises one or more computer program code portions for carrying out one or more operations according to any one of the embodiments of FIGS. 2 to 13 or operations thereof.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chipset (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program or portions thereof. Embodiments of the methods described in connection with FIGS. 2 to 13 may be carried out by executing at least one portion of a computer program comprising corresponding instructions. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. The computer program medium may be a non-transitory medium. Coding of software for carrying out the embodiments as shown and described is well within the scope of a person of ordinary skill in the art.

It will be obvious to a person skilled in the art that, as the technology advances, the inventive concept can be implemented in various ways. The invention and its embodiments are not limited to the examples described above but may vary within the scope of the claims.

The invention claimed is:

1. A method for estimating a cardiovascular status of a user in a wrist computer, the method comprising:
   synchronizing a clock of the wrist computer and a clock of an external electrocardiogram sensor device to a common clock;
   detecting, in a first measurement signal received by the wrist computer in one or more frames from the electrocardiogram sensor adapted to be attached to a first location of the user's body, a first occurrence of a blood pulse wave, the frames being in accordance with a wireless communication protocol;
   detecting, in a second measurement signal measured by a photoplethysmogram sensor comprised in the wrist computer from the user's wrist, a second occurrence of the blood pulse wave;
   estimating, on the basis of said detections synchronized to the common clock, time characteristics of the blood pulse wave;
   computing, on the basis of said time characteristics, a metric representing the cardiovascular status of the user;
   providing an altitude sensor with the wrist computer;
   using the altitude sensor to determine that the photoplethysmogram sensor is at a determined reference altitude at a time of detecting the second measurement signal; and
   computing the metric only under a condition where the photoplethysmogram sensor is at the determined reference altitude at the time of detecting the second measurement signal.

2. The method of claim 1, wherein an electrode of the electrocardiogram sensor is provided in a form of a transparent film on a display screen of the wrist computer, and wherein the photoplethysmogram sensor is provided on an opposite side of the wrist computer with respect to the electrocardiogram sensor.

3. The method of claim 1, wherein the reference altitude is received from the electrocardiogram sensor device attached to the user's chest.

4. The method of claim 3, wherein the altitude sensor is comprised in the wrist computer, the method further comprising calibrating the altitude sensor of the wrist computer with an altitude sensor of the electrocardiogram sensor device by instructing the user to bring the wrist computer to touch the electrocardiogram sensor device, to communicate an altitude between the wrist computer and the electrocardiogram sensor device, and thus calibrating the altitude sensor to a same altitude.

5. The method of claim 1, wherein the first measurement signal is received from the electrocardiogram sensor device via the user's skin through an electrode of the wrist computer attached to the user's skin.

6. The method of claim 1, wherein said synchronizing is performed by using clock synchronization of a wireless communication protocol.

7. A wrist computer for estimating a cardiovascular status of a user comprising:
- a photoplethysmogram sensor; and
- a processing circuitry configured to perform operations comprising:
- synchronizing a clock of the wrist computer and a clock of an external electrocardiogram sensor device to a common clock;
- detecting, in a first measurement signal received in one or more frames from the electrocardiogram sensor adapted to be attached to a first location of the user's body, a first occurrence of a blood pulse wave, the frames being in accordance with a wireless communication protocol;
- detecting, in a second measurement signal acquired from the photoplethysmogram sensor, a second occurrence of the blood pulse wave;
- estimating, on the basis of said detections synchronized to the common clock, time characteristics of the blood pulse wave; and
- computing, on the basis of said time characteristics, a metric representing the cardiovascular status of the user, the wrist computer further comprising an altitude sensor, wherein the processing circuitry is configured to use the altitude sensor to determine that the photoplethysmogram sensor is at a determined reference altitude at a time of detecting the second measurement signal, and to compute the metric only under a condition where the photoplethysmogram sensor is at the determined reference altitude at the time of detecting the second measurement signal,
- the photoplethysmogram sensor, a second occurrence of the blood pulse wave;
- estimating, on the basis of said detections synchronized to the common clock, time characteristics of the blood pulse wave; and
- computing, on the basis of said time characteristics, a metric representing the cardiovascular status of the user, the wrist computer further comprising an altitude sensor, wherein the processing circuitry is configured to use the altitude sensor to determine that the photoplethysmogram sensor is at a determined reference altitude at a time of detecting the second measurement signal, and to compute the metric only under a condition where the photoplethysmogram sensor is at the determined reference altitude at the time of detecting the second measurement signal.

8. The wrist computer of claim 7, the wrist computer further comprising a display screen, wherein an electrocardiogram sensor electrode is provided in a form of a transparent film on the display screen of the wrist computer, and wherein the photoplethysmogram sensor is provided on an opposite side of the wrist computer with respect to the electrocardiogram sensor electrode.

9. The wrist computer of claim 7, wherein the processing circuitry is configured to receive the reference altitude from the electrocardiogram sensor device external to the wrist computer.

10. The wrist computer of claim 9, wherein the processing circuitry is configured to calibrate the altitude sensor of the wrist computer with an altitude sensor of the electrocardiogram sensor device by instructing the user to bring the wrist computer to touch the electrocardiogram sensor device, to communicate an altitude between the wrist computer and the electrocardiogram sensor device, thus calibrating the altitude sensor to a same altitude.

11. The wrist computer of claim 7, wherein the first measurement signal is received from the electrocardiogram sensor device via the user's skin through an electrode of the wrist computer adapted to be attached to the user's skin.

12. The wrist computer of claim 7, wherein said synchronizing is performed by using clock synchronization of a wireless communication protocol.

13. A computer program product embodied on a non-transitory computer-readable medium readable by a computer and, when executed by the computer, configured to cause the computer to execute a computer process comprising:
- synchronizing a clock of a wrist computer and a clock of an external electrocardiogram sensor device to a common clock;
- detecting, in a first measurement signal received in one or more frames from the electrocardiogram sensor adapted to be attached to a first location of the user's body, a first occurrence of a blood pulse wave, the frames being in accordance with a wireless communication protocol;
- detecting, in a second measurement signal measured by a photoplehysmogram sensor comprised in the wrist computer from the user's wrist, a second occurrence of the blood pulse wave;
- estimating, on the basis of said detections synchronized to the common clock, time characteristics of the blood pulse wave;
- computing, on the basis of said time characteristics, a metric representing the cardiovascular status of the user;
- providing an altitude sensor with the wrist computer;
- using the altitude sensor to determine that the photoplethysmogram sensor is at a determined reference altitude at a time of detecting the second measurement signal; and
- computing the metric only under a condition where the photoplethysmogram sensor is at the determined reference altitude at the time of detecting the second measurement signal.

* * * * *